(12) United States Patent
Mobarak

(10) Patent No.: US 8,425,886 B2
(45) Date of Patent: Apr. 23, 2013

(54) STABLE SOLID DEODORANT PRODUCT AND METHOD FOR MANUFACTURING SAME

(75) Inventor: Hany Abo-El-Magd Mobarak, Milton (CA)

(73) Assignee: Knowlton Development Corporation, Inc., Knowlton (CA)

( * ) Notice: Subject to any disclaimer, the term of this patent is extended or adjusted under 35 U.S.C. 154(b) by 20 days.

(21) Appl. No.: 13/272,736

(22) Filed: Oct. 13, 2011

(65) Prior Publication Data

US 2012/0034179 A1    Feb. 9, 2012

Related U.S. Application Data

(63) Continuation of application No. 12/538,379, filed on Sep. 11, 2009, now abandoned.

(30) Foreign Application Priority Data

Aug. 10, 2009   (CA) ..................................... 2675184

(51) Int. Cl.
*A61Q 15/00* (2006.01)
*A61K 8/00* (2006.01)

(52) U.S. Cl.
USPC ............................................. 424/65; 424/401

(58) Field of Classification Search ........................ None
See application file for complete search history.

(56) References Cited

U.S. PATENT DOCUMENTS

| 4,252,789 | A | * | 2/1981 | Broad | 424/65 |
| 4,822,602 | A | * | 4/1989 | Sabatelli | 424/65 |
| 4,863,721 | A | * | 9/1989 | Beck et al. | 424/47 |
| 2005/0089488 | A1 | * | 4/2005 | Kim | 424/65 |
| 2005/0271609 | A1 | * | 12/2005 | Fei et al. | 424/65 |
| 2007/0202062 | A1 | * | 8/2007 | Workman et al. | 424/66 |

FOREIGN PATENT DOCUMENTS

WO    WO 2004039344    *    5/2004

OTHER PUBLICATIONS

Jason Natural Deodorant Stick. http://www.healthpost.co.nz/Product/JNDTTS/Tea-Tree-Deodorant-Stick.*
Nutribiotic. http://www.nutribiotic.com/mango-melon-deodorant.html. Archived Apr. 12, 2008. Accessed Jan. 24, 2010.*
Deodorant & Antiperspirant Formulary. Cosmetics and Toiletries. 1985. vol. 100. pp. 65-75.*
Cetearyl Alcohol. http://www.theherbarie.com/Cetearyl-Alcohol-NF-pr-89.html. Nov. 23, 2006. Accessed Feb. 8, 2011.*
Baking Soda Deodorant Issues. http://naturalliving.livejournal.com/4536121.html. Published Jul. 9, 2008.*
LifeHacker. http://lifehacker.com/5239562/display-the-date-a-webpage-was-published-in-search-results. Published. May 4, 2009.*

* cited by examiner

Primary Examiner — David J Blanchard
Assistant Examiner — Lori K Mattison
(74) Attorney, Agent, or Firm — Gowling Lafleur Henderson LLP

(57) ABSTRACT

The present invention provides a deodorant formulation having improved efficacy and stability. The deodorant formulation comprises propanediol, ethylhexylglycerin, and grapefruit seed extract as the principal deodorizing actives. The combination of these deodorizing active ingredients results in a formulation with strong efficacy. The deodorant formulation of the invention may further be formed into a stable solid stick product in accordance with the methods outlined herein.

7 Claims, 9 Drawing Sheets

FIGURE 1

Sample Formulation

| Material | % |
|---|---|
| Propanediol | 45.00% |
| Behenyl Alcohol | 0.10% |
| Cetearyl Alcohol and Cetearyl Glucoside | 0.01-0.3% |
| Disstarch Phosphate Acetate | 0.01-0.9% |
| Ethylhexylglycerin | 0.60% |
| Glycerin | 20.00% |
| Grapefruit Seed Extract | 0.90% |
| Hydroxyethylcellulose | 0.05% |
| Sodium Bicarbonate | 0.01% |
| Sodium Chloride | 0.05% |
| Sodium Stearate | 4.0% |
| Water | 28.0% |
| Additives | q.s. |
| Essential Oil / Perfume | q.s. |
| | 100.00% |

FIGURE 2

Efficacy Panel Test – 7 Point Odor Grading Scale

Positive                          Neutral                          Negative

| 1 | 2 | 3 | 4 | 5 | 6 | 7 |
|---|---|---|---|---|---|---|
| Very Strong pleasant odor | Medium-strong pleasant odor | Mild-faint pleasant odor | No detectable odor positive or negative | Mild-faint unpleasant odor | Medium-strong unpleasant odor | Repulsive unpleasant odor |

Average Odor Scores for Treated v. Control

Treated

| $T_0$ | 2 minutes post-treatment | 8 Hours post-treatment | 24 hours post-treatment |
|---|---|---|---|
| 5.1 | 3.6 | 4.4 | 5.0 |

Control

| $T_0$ | 2 minutes post-treatment | 8 Hours post-treatment | 24 hours post-treatment |
|---|---|---|---|
| 5.0 | 4.8 | 4.8 | 5.1 |

FIGURE 4

12-Week Stability Test Results at 4°C, 25°C, and 45°C for Top Filled, Flat Finish Deodorant Test Temperature: 4°C
Fill Style: Top Fill: Flat

| Week | 0 | 1 | 2 | 3 | 4 | 5 | 6 | 7 | 8 | 9 | 10 | 11 | 12 |
|---|---|---|---|---|---|---|---|---|---|---|---|---|---|
| Weight (g) | 81.68 | 81.54 | 81.47 | 81.37 | 81.37 | 81.39 | 81.37 | 81.37 | 81.41 | 81.42 | 81.43 | 81.46 | 81.39 |
| % Weight Loss | 0.00% | 0.17% | 0.26% | 0.38% | 0.38% | 0.36% | 0.38% | 0.38% | 0.33% | 0.32% | 0.31% | 0.27% | 0.36% |

Test Temperature: 25°C
Fill Style: Top Fill: Flat

| Week | 0 | 1 | 2 | 3 | 4 | 5 | 6 | 7 | 8 | 9 | 10 | 11 | 12 |
|---|---|---|---|---|---|---|---|---|---|---|---|---|---|
| Weight (g) | 86.47 | 86.38 | 86.29 | 86.19 | 85.95 | 85.70 | 85.46 | 85.24 | 85.03 | 84.80 | 84.59 | 84.38 | 84.22 |
| % Weight Loss | 0.00% | 0.10% | 0.21% | 0.32% | 0.60% | 0.89% | 1.17% | 1.42% | 1.67% | 1.93% | 2.17% | 2.42% | 2.60% |

Test Temperature: 45°C
Fill Style: Top Fill: Flat

| Week | 0 | 1 | 2 | 3 | 4 | 5 | 6 | 7 | 8 | 9 | 10 | 11 | 12 |
|---|---|---|---|---|---|---|---|---|---|---|---|---|---|
| Weight (g) | 86.85 | 86.66 | 86.52 | 86.41 | 86.05 | 85.67 | 85.33 | 84.97 | 84.57 | 84.12 | 83.73 | 83.34 | 83.00 |
| % Weight Loss | 0.00% | 0.22% | 0.38% | 0.51% | 0.92% | 1.36% | 1.75% | 2.16% | 2.63% | 3.14% | 3.59% | 4.04% | 4.43% |

FIGURE 5

12-Week Stability Test Results at 4°C, 25°C, and 45°C for Top Filled, Dome Finish Deodorant Test Temperature: 4°C
Fill Style: Top Fill: Dome

| Week | 0 | 1 | 2 | 3 | 4 | 5 | 6 | 7 | 8 | 9 | 10 | 11 | 12 |
|---|---|---|---|---|---|---|---|---|---|---|---|---|---|
| Weight (g) | 82.83 | 82.73 | 82.70 | 82.64 | 82.63 | 82.65 | 82.54 | 82.55 | 82.61 | 82.63 | 82.64 | 82.68 | 82.52 |
| % Weight Loss | 0.00% | 0.12% | 0.16% | 0.23% | 0.24% | 0.22% | 0.35% | 0.34% | 0.27% | 0.24% | 0.23% | 0.18% | 0.37% |

Test Temperature: 25°C
Fill Style: Top Fill: Dome

| Week | 0 | 1 | 2 | 3 | 4 | 5 | 6 | 7 | 8 | 9 | 10 | 11 | 12 |
|---|---|---|---|---|---|---|---|---|---|---|---|---|---|
| Weight (g) | 83.08 | 83.03 | 82.92 | 82.85 | 82.73 | 82.58 | 82.56 | 82.47 | 82.23 | 82.09 | 81.94 | 81.80 | 81.80 |
| % Weight Loss | 0.00% | 0.06% | 0.19% | 0.28% | 0.42% | 0.60% | 0.63% | 0.73% | 1.02% | 1.19% | 1.37% | 1.54% | 1.54% |

Test Temperature: 45°C
Fill Style: Top Fill: Dome

| Week | 0 | 1 | 2 | 3 | 4 | 5 | 6 | 7 | 8 | 9 | 10 | 11 | 12 |
|---|---|---|---|---|---|---|---|---|---|---|---|---|---|
| Weight (g) | 76.60 | 76.46 | 76.37 | 76.22 | 75.93 | 75.59 | 75.28 | 74.94 | 74.69 | 74.31 | 73.97 | 73.64 | 73.38 |
| % Weight Loss | 0.00% | 0.18% | 0.30% | 0.50% | 0.87% | 1.32% | 1.72% | 2.17% | 2.49% | 2.99% | 3.43% | 3.86% | 4.20% |

FIGURE 6

12-Week Stability Test Results at 4°C, 25°C, and 45°C for Bottom-Filled Deodorant Test Temperature: 4°C
Fill Style: Bottom Fill

| Week | 0 | 1 | 2 | 3 | 4 | 5 | 6 | 7 | 8 | 9 | 10 | 11 | 12 |
|---|---|---|---|---|---|---|---|---|---|---|---|---|---|
| Weight (g) | 109.06 | 108.98 | 108.86 | 107.02 | 106.77 | 106.91 | 106.82 | 106.88 | 106.69 | 106.82 | 106.91 | 107.02 | 106.93 |
| % Weight Loss | 0.00% | 0.07% | 0.18% | 1.87% | 2.10% | 1.97% | 2.05% | 2.00% | 2.17% | 2.05% | 1.97% | 1.87% | 1.95% |

Test Temperature: 25°C
Fill Style: Bottom Fill

| Week | 0 | 1 | 2 | 3 | 4 | 5 | 6 | 7 | 8 | 9 | 10 | 11 | 12 |
|---|---|---|---|---|---|---|---|---|---|---|---|---|---|
| Weight (g) | 129.83 | 128.80 | 128.27 | 126.69 | 125.85 | 125.10 | 124.40 | 123.76 | 123.22 | 122.52 | 121.90 | 121.29 | 120.77 |
| % Weight Loss | 0.00% | 0.79% | 1.20% | 2.42% | 3.07% | 3.64% | 4.18% | 4.68% | 5.09% | 5.63% | 6.11% | 6.58% | 6.98% |

Test Temperature: 45°C
Fill Style: Bottom Fill

| Week | 0 | 1 | 2 | 3 | 4 | 5 | 6 | 7 | 8 | 9 | 10 | 11 | 12 |
|---|---|---|---|---|---|---|---|---|---|---|---|---|---|
| Weight (g) | 123.50 | 122.02 | 121.07 | 120.15 | 119.05 | 117.73 | 116.72 | 115.64 | 114.83 | 113.86 | 113.04 | 112.24 | 111.68 |
| % Weight Loss | 0.00% | 1.20% | 1.97% | 2.71% | 3.60% | 4.67% | 5.49% | 6.36% | 7.02% | 7.81% | 8.47% | 9.12% | 9.57% |

STABLE SOLID DEODORANT PRODUCT AND METHOD FOR MANUFACTURING SAME

CROSS-REFERENCE TO RELATED APPLICATIONS

This application is a continuation application of U.S. application Ser. No. 12/538,379, filed Sep. 11, 2009, now abandoned, which claimed priority from Canadian Patent Application No. 2,675,184, filed Aug 10, 2009, the contents of which are incorporated herein by reference.

FIELD OF THE INVENTION

The present invention relates to a novel solid deodorant formulation, and a method for manufacturing a deodorant stick product having excellent stability and efficacy.

BACKGROUND OF THE INVENTION

Topical deodorant formulations for use in controlling odour in the underarm area have been available in the market for many years, in solid stick or liquid form. Deodorant compositions have contained deodorizing active ingredients of several types. For example, antimicrobial agents function to inhibit bacterial growth, thus reducing bacterial interactions with sweat gland secretions, which are responsible for producing undesirable odours. Malodour masking agents such as perfumes and fragrances function to mask the malodours produced by bacterial interactions. Malodour neutralizers are also available which serve to chemically fix malodours. Thus, deodorant actives known in the art have generally referred to topical materials which inhibit the formation of, mask, or neutralize malodours resulting from perspiration.

Solid deodorant formulations of the prior art have commonly contained propylene glycol as the principal ingredient, and triclosan as a deodorizing active. The general manufacturing process for solid deodorants and cosmetics is also known. Deodorant formulations are typically mixed in relatively large quantities under heat, then poured into individual product containers, which act as molds to permit the sticks to be cast directly in them. Such product containers may be filled from the bottom or the top, and the deodorant stick may be shaped with a domed top or flat top.

A problem with many of the deodorant formulations that form part of the prior art is that they have relied on ingredients that have been found to be detrimental to human health or irritating to the skin. For instance, as substantiated by independent studies, a common deodorizing active material, triclosan, appears to be harmful to human skin and potentially carcinogenic. Another common and effective ingredient in deodorant formulations, propylene glycol, has been found to be irritating to many consumers with sensitive skin. As consumers become more conscious of the ingredients contained in personal care products such as deodorants, there has been rising demand for alternative formulations which are composed of ingredients that are naturally sourced or are formulated with minimal environmental impact, are not detrimental to human health, and which are mild when applied to skin and can therefore be used by a greater number of consumers, even those with sensitive skin.

In addition to the above needs in regard to deodorant formulations, a significant manufacturing issue with deodorant formulations that rely on natural ingredients and do not contain triclosan or propylene glycol is reduced stability and shelf life. When solid stick formulations are created, a problem frequently encountered has been the shrinking of the deodorant stick after it has been poured into the container. Natural deodorant formulations in particular have been plagued by the problem of the stick shrinking at ambient temperatures, such that the deodorant stick separates from the container wall. This problem with solid cosmetic formulations is known in the industry as "sweating", whereby moisture from the solid deodorant stick formulation condenses on the surface of the stick, and ultimately evaporates. As it evaporates, the product shrinks back from the container edges and loses the original surface texture. This results in an unattractive and unsalable product with poor surface characteristics. It has been a significant and costly problem with many natural deodorant stick products.

The problem is believed to reside in the use of water and volatile alcohols in the natural deodorant formulation, which has arisen in prior art formulations, including those formulated to lack propylene glycol. When such ingredients form a significant portion of the solid formulation, it is difficult to prevent these ingredients from condensing out of the solid stick and evaporating. However, in formulating natural and substantially natural deodorant formulations in accordance with prior art teachings, it has been inevitable that the high percentage of water and volatile alcohols causes such stability problems.

What is needed is a solid stick deodorant formulation, that preferably contains all natural or naturally sourced ingredients, and is stable once formed into a deodorant stick product in a container.

SUMMARY OF THE INVENTION

The present invention provides a natural deodorant formulation that exhibits excellent efficacy, at levels beyond those seen for other such formulations available in the prior art. Further, the formulation of the present invention exhibits improved stability once formed into a deodorant stick product in a container that is filled from the top opening compared with a bottom filled container. This product addresses the above-mentioned drawbacks of solid natural deodorant formulations and provides for a product with increased stability and therefore increased shelf life and commercial value.

In one embodiment the invention comprises a novel deodorant formulation having propanediol as the base, combined with the deodorizing active materials ethylhexylglycerin and grapefruit seed extract. It has been found that the combination of propanediol, grapefruit seed extract and ethylhexylglycerin, when applied topically to the skin, provides improved deodorant efficacy, that is greater than the additive deodorant benefits that would otherwise be expected from such a combination. When manufactured into solid stick deodorant product in a container in accordance with the process outlined herein, a deodorant stick product displaying excellent efficacy and stability is formed.

The present invention is further directed to a novel manufacturing method for making and forming deodorant products in accordance with the described formulations.

The present invention is also directed to a stable and efficaceous deodorant stick product manufactured in accordance with the specified method and in accordance with the claimed formulations.

BRIEF DESCRIPTION OF THE FIGURES

The present invention will now be better understood with reference to the description and to the accompanying figures in which:

FIG. 1 is a table outlining a sample deodorant stick formulation in accordance with the invention;

FIG. 2 is a table summarizing the efficacy results obtained with the deodorant formulation described in FIG. 1, as compared to a control formulation;

FIG. 4 consists of comparative tables showing the results of a 12-week stability test at each of 4° C., Room Temperature (25° C.), and 45° C. for a top filled, domed deodorant product made in accordance with the formula in FIG. 1;

FIG. 5 consists of comparative tables showing the results of a 12-week stability test at each of 4° C., Room Temperature (25° C.), and 45° C. for a top filled, flat-finish deodorant product made in accordance with the formula in FIG. 1;

FIG. 6 consists of comparative tables showing the results of a 12-week stability test at each of 4° C., Room Temperature (25° C.), and 45° C. for a bottom filled deodorant product made in accordance with the formula in FIG. 1;

DETAILED DESCRIPTION OF THE PREFERRED EMBODIMENTS

Figure 3:
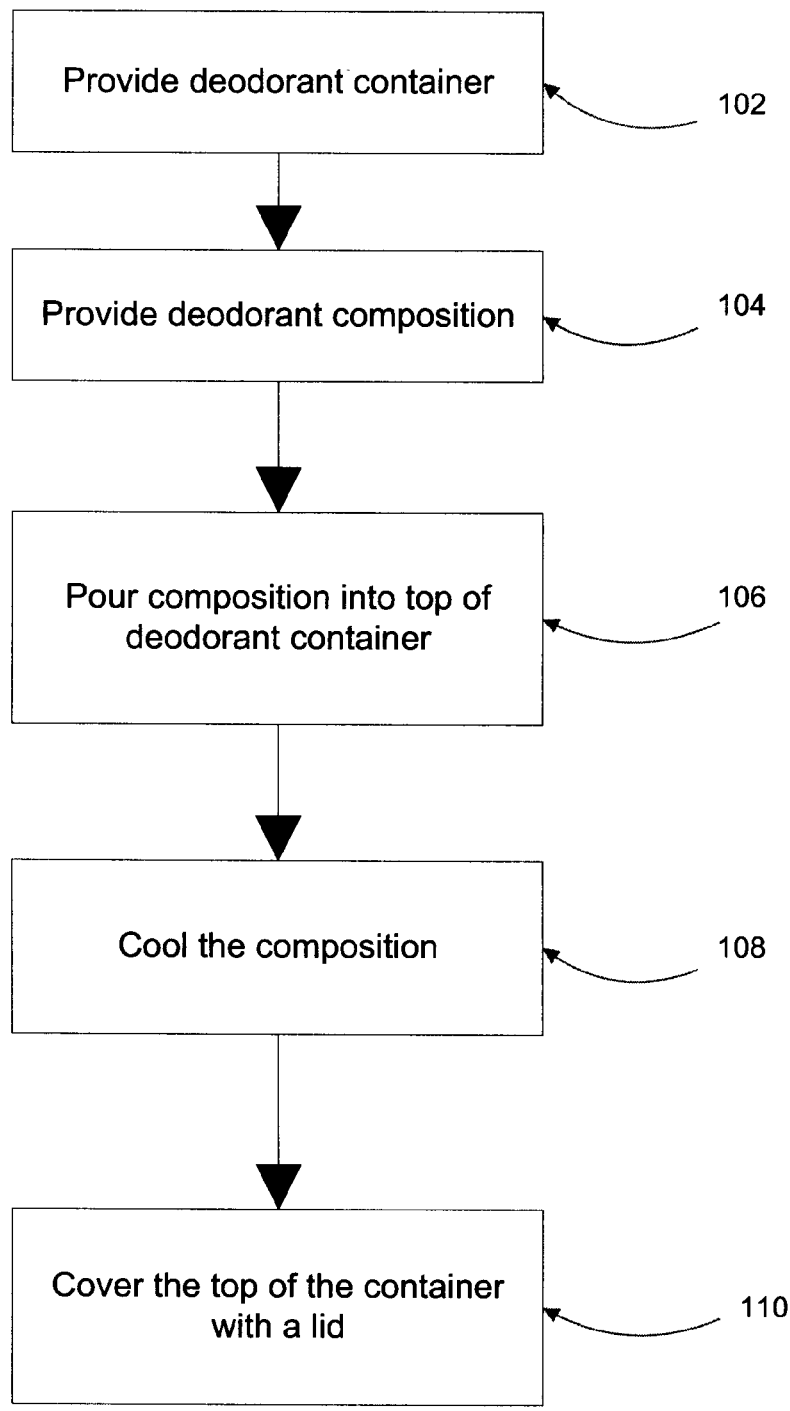
FIG. 3 is a flowchart showing an exemplary embodiment of a method of manufacturing a deodorant stick product in accordance with one aspect of the present invention.

The present invention relates to a deodorant composition or formulation that shows remarkable qualities of stability once formed into a solid stick product in accordance with the manufacturing method described herein. The solid stick product made in accordance with the formulation of the invention may be formulated to be clear, translucent, or substantially opaque in appearance. It is preferably clear or translucent.

The ingredients used in the deodorant composition of the invention are preferably natural, or substantially natural, ingredients. In the deodorant industry, the term "natural" indicates that the ingredient is derived from a plant or animal source. This is in contrast to synthetically derived chemicals which cannot typically be considered to be "natural" ingredients.

In a first embodiment, the deodorant composition comprises propanediol (chemical name: 1,3-propanediol), combined with further deodorizing active ingredients, namely ethylhexylglycerin and grapefruit seed extract. Each of these ingredients are known in the art and available from a number of sources. For example, the propanediol used is commercially available from DUPONT™ under the trade-mark ZEMEA™. ZEMEA™ is particularly beneficial to use in a natural deodorant formulation as it is a biodegradable product that is manufactured from corn with reduced environmental impact, using 40% less energy in the manufacturing process as compared with a petroleum-based propanediol.

Ethylhexylglycerin is a known deodorizing active ingredient, which is a representative of the 1-alkyl glycerin ethers, and which operates to inhibit the growth and multiplication of malodour-causing bacteria. Substances with a similar structure to ethylhexylglycerin occur in nature. Grapefruit seed extract is also a known deodorizing active ingredient, which is made by converting grapefruit seeds and pulp into acidic liquid. The resulting extract is effective as an antibacterial agent.

There are hundreds of options for deodorizing active ingredients for use in cosmetic formulations such as stick deodorants. While each of the above ingredients are known generally to have activity as deodorizing agents, they have not been known to stand out as particularly effective deodorizing agents as compared to other available agents. However, as detailed below, the combination of the above three ingredients in a deodorant composition gives unexpectedly high levels of deodorant activity, which is long-lasting. Such levels have not been seen in the prior art deodorant formulations lacking propylene glycol and triclosan.

In addition to the above three deodorizing active ingredients, additional ingredients may be incorporated in the deodorant formulation. For example, vegetable glycerin may be included as a solvent ingredient for water-soluble components of the formulation, and to contribute structure to the solidified product. In addition to propanediol, other polymeric or nonpolymeric alcohols may be included. Other ingredients that may be used, include but are not limited to, quantities of diethylene glycol, triethylene glycol, dipropylene glycol, tripropylene glycol, tetrapropylene glycol, tetraethylene glycol, dibutylene glycol, diethylene glycol, monoethylether, PEG-8, 1,3-butanediol, 1,4-butanediol, glycerol propoxylate, dipropylene glycol, tripropylene glycol, tetrapropylene glycol, hexylene glycol, 1,2-hexanediol, 1,3-butylene glycol, 1,2,6-trihyroxyhexane, 1,2,3-trihydroxyhexane, hexylene glycol, and 1,2-henediol.

Another ingredient that may be included is a gelling agent. Gelling agents are also known as structurants. A particularly preferred and common gelling agent used in solid deodorant formulations is sodium stearate. Other optional gelling agents which may be used include, but are not limited to: glyceryl laurate, beeswax, colloids, cocoa butter, shea butter, mango butter, hydrogenated vegetable oils, sodium oleate, sodium palmitate, sodium laurate, sodium arachidate, sodium behenate, potassium stearate, potassium palmitate, sodium myristate, aluminum monostearate, 16-hydroxyhexadecanoyl acid, fatty acid amides, fatty acid alkanol amides, dibenzalsorbitol, alkyl amides of citric acids, tricarballylic acid, aconitic acid, nitrilotriacetic acid, succinic acid, 2-hydroxy-1,2,3-propane tributylamide, 1-propene-1,2,3-trioctylamide, N,N',N"-tri (acetodecylamide) amine, 2-dodecyl-N, N'-dihexylsuccinamide, 2-dodecyl-N,N'-dibutylsuccinamide, dimethylamine stearate, triethylamine stearate, triethylemine oleate, diethylamine stearate, and trimethylamine oleate.

Emulsifiers may also be included in the formulation. For instance, non-volatile saturated fatty alcohols such as behenyl alcohol, also known as docosanol, may be included. Also useful as emulsifiers are cetearyl alcohol and cetearyl glucoside. Other emulsifiers available for use for this application include, but are not limited to: inulin lauryl carbamate, citric acid esters, polyglycerol esters of fatty acids, sorbitan esters of fatty acids, saponins, lecithins, and carageenan.

Thickening agents may also be included in the formulation, to increase viscosity. For instance, known thickening agents that may be used in this application include, but are not limited to, sodium chloride, hydroxyethylcellulose, carbomer, polyethylene glycol, vegetable gums, waxes, and petroleum jelly.

Starch may also be added to the formulation, principally to improve the texture and feel of the solid product. Types of starch that may be used in the formulations of the invention include, but are not limited to, corn (*Zea Mays*) starch and distarch phosphate acetate.

Additional deodorizing actives may be included with the three actives specified above. For example, sodium bicarbonate is a known ingredient with deodorizing properties. There are hundreds of other ingredients with such properties, including, but not limited to: alpha bisabolol, benzoic acid, rosemarinic acid, caffeic acid, carnosic acid, ferrulic acid, galic acid, perillic acid, glucose methyl rapesseedate ferment, C12-13 alkyl lactate, chitosan, hinokitiol, eucalyptol, linalool, limonene, geraniaol, citral, benzyl benzoate, citronellol, sodium citronellate, citronellyl methylcrotonate, coumarin, engenool, benzyl salicylate, alum, farnesol, glucose oxidase, lactoperoxidase, glycerin monolaurate, levulinic acid, nisin, phenoxyethanol, potassium sorbate, isostearic acid, sodium usnate, tea tree, cetyltrimethylammonium bromide, cetyl pyridinium chloride, benzethonium chloride, diisobutyl phenoxy ethoxy ethyl dimeethyl benzyl ammonium chloride, sodium N-palmethyl sarcosine, N-myristoyl glycine, potassium N-lauryl sarcosine, trimethyl ammonium chloride, sodium aluminum chlorohydroxy lactate, triethyl citrate, triclocarban, diaminoalkyl amides such as L-lysine hexadecyl amide, heavy metal salts of citrate, salicylate, and piroctose, polyglyceryl-3-caprylate, zinc phenolsulfate, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmetoyl sarcosine, lauroyl sarcosine, N-myristoyl glycine, potassium N-lauroyl sarcosine, stearyl trimethyl ammonium chloride, cetyltrimethyalammonium chloride, cetylpyridinium chloride, diisobutylethyoxyethyldimenethylbenzelammonium chloride, sodium N-laurylsarcosinate, sodium-N-palmethylsarcosinate, N-myristoylglycine, potassium N-laurylsarcosine, trimethylammonium chloride, sodium aluminum chlorohydroxylactate, triethyl citrate, tricetylmethylammonium chloride, triclosan, phenoxyethanol, 1,5-pentanediol, 1,6-hexandediol, diaminoalkylamide (eg. 1-lysine hexadecyl amide, citrate heavy metal sales, salicylates, piroctoses, zinc ricinoleate, zinc phenolsulfonate, dichloro-m-xylenol, 2,2'-methylenebis(3,4,6-trichlorophenol), 2,2'-thiobis(4,6-dichloropheol), p-chloro-m-zelenol, dichloro-m-xylenol, phenethyl alcohol, and any of the alkalirhodanides.

In addition, other malodor masking agents such as perfumes and fragrances may be incorporated. Again, there are many options known in the art that have been used in cosmetic formulations, and which include, but are not limited to: any essential oils or perfumes such as florals, herbs, fruits, trees, shrubs, fungi, corals, grasses such as rosewood, lavender, litsea cubeba, tea tree, lemon, lime, orange, petitgrain, geranium, lemongrass, palmarosa, mandarin, coriander, rose, patchouli, yarrow, cypress, cedar, citronella, bergamot, pine, myrtle, cypress, orange blossom, pine oil, citrus oil, jasmine oil, lily oil, rose oil, ylang ylang oil, sage oil, chamomile oil, oil of cloves, Melissa oil, mint oil, cinnamon leaf oil, lime blossom oil, juniper berry oil, vetiver oil, iolibanum oil, galbanum oil, laudanum oil, resins such as benzoin siam resinoid and opoponax resinoid, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycinate, allyl cyclohexylpropionate, styrallyl propionate, benzyl salicylate, benzyl ethyl ether, citral, citronellal, citronellyloxyacetaldehyde, cyclamenaldehyde, hydroxycitronellal, lilial, bourgeonal, ionones, anethole, citronellol, eugenool, geraniol, linalool, phenylethyl alcohol, terpineol, isoamyl salicylate, benzyl salicylate, thyme oil red, B-methyl naphthyl ketone, p-t-butyl-A-methyl hydrocinnamic aldehyde, p-t-amyl cyclohexanone, coumarin, B-naphthyl methyl ether, diethyl phthalate, phenylethyl phenylacetate, dimurcetol, phenylethyl alcohol, undecyl aldehyde, undecylenic aldehyde, lauric aldeheyde, amyl cinnamic aldehyde, ethyl methyl phenyl glycidate, methyl nonyl aldehyde, octyl aldehyde, undecalactone, hexyl cinnamic aldehyde, benzaldehyde, vanillin, heliotropine, camphor, para-hydroxy phenolbutannone, 6-acetyl 1,1,3,4,4,6 hexamethyl tetrahydronaphtahalene, alpha-methyl ionone, gamma-methyl ionone, amyl-cyclohexanone, linalyl acetate, isopropyl mystirate, cedryl acetate, and myrcenyl acetate.

It is further noted that varying the amounts of certain ingredients can result in alterations to the appearance of the final solid product, but have not been found to impact the performance of the product or its stability. For instance, as shown in FIG. 1, ranges are provided for the respective amounts of starch and the cetearyl alcohol/cetearyl glucoside. The product of the invention may be given a transparent appearance by using cetearyl alcohol/cetearyl glucoside in an amount closer to the upper end of the range, in combination with an amount of starch provided closer to the lower end of the range. Similarly, if a translucent product is desired, cetearyl alcohol/cetearyl glucoside may be incorporated in an amount closer to the lower end of the range, in combination with an amount of starch provided closer to the upper end of the range. Clarity of the formulation may be further enhanced by including known clarifying agents such as sodium bicarbonate.

As will be understood from the description provided herein, in one embodiment the present invention provides a deodorant formulation comprising by weight, based on the total weight of the composition: from about 40-70% propanediol; from about 0.1-1% ethylhexylglycerin; and from about 0.5-2% grapefruit seed extract. It will be understood that the use of the term "about" in relation to a range applies to both ends of the range provided.

In another embodiment, the deodorant formulation further comprises at least one of a gelling agent, a thickening agent, an emulsifier, starch, a clarifying agent, further deodorizing active ingredients, and mixtures thereof.

In an alternative embodiment, the deodorant formulation comprises, by weight based on the total weight of the composition: from about 40-70% propanediol; from about 0.1-1% ethylhexylglycerin; from about 0.5-2% grapefruit seed extract; from about 2-10% gelling agent; from about 0.1-1% thickening agent; from about 0.1-1% of an emulsifier; from about 0.01-2% starch; from about 0.01-0.1% of a clarifying agent; and from about 0.001-5% of one or more further deodorizing active ingredients.

In a further embodiment, the deodorant formulation comprises, by weight based on the total weight of the composition: from about 40-70% propanediol; from about 0.1-1% ethylhexylglycerin; from about 0.5-2% grapefruit seed extract; from about 2-10% sodium stearate; from about 0.1-1% hydroxyethylcellulose; from about 0.1-1% sodium chloride; from about 0.1-1% behenyl alcohol; from about 0.1-1% cetearyl alcohol, from about 0.1-1% cetearyl glucoside, from about 0.01-2% distarch phosphate acetate; from about 0.01-2% corn starch, from about 0.01-0.1% of sodium bicarbonate; about 20-30% water; and from about 0.001-5% of one or more further deodorizing active ingredients.

In an alternative embodiment, the deodorant formulation comprises, by weight based on the total weight of the composition: about 45% propanediol; about 0.6% ethylhexylglycerin; about 0.9% grapefruit seed extract; from about 0.01-0.3% cetearyl alcohol, cetearyl glucoside or mixtures thereof;

from about 0.01-0.9% distarch phosphate acetate; about 0.10% behenyl alcohol; about 0.05% hydroxyethylcellulose; about 20% glycerin; about 0.01% sodium bicarbonate; about 0.05% sodium chloride; about 4% sodium stearate; about 28% water; and additives, essential oils and/or perfume q.s.

A sample formulation of the invention, as shown in FIG. 2, displays excellent efficacy. In the industry, efficacy testing for deodorants is typically conducted by way of panel studies, in which the test substances and control substances are applied to the axilla of human subjects, and odour is then assessed at intervals by an objective panel of reviewers. This type of deodorant testing is referred to in the industry as a "sniff test". Such a sniff test was conducted in this case, involving twenty subjects and three judges.

As seen in FIG. 2, the twenty subjects were tested using a 7-point subjective axillary odour scale, with a ranking of 1 indicating a pleasant odour, and a ranking of 7 indicating a strong unpleasant odour. A middle ranking of 4 indicated no detectable odour, positive or negative.

Subjects were tested prior to treatment to establish a baseline, and at intervals of 2 minutes, and 8 hours post-treatment. The mean results for the twenty subjects are presented in FIG. 2. The values demonstrate that the deodorant formulation of the invention was effective at neutralizing axillary odour, such that even at 8 hours post-treatment, the averaged odour rating of the subjects was close to neutral. The differences between treated subjects and control subjects were found to be statistically significant.

The panel testing results summarized in FIG. 2 show 8 hour efficacy for the deodorant formulation of the invention. This level of efficacy is excellent, and has not been seen for a deodorant formulation containing substantially natural ingredients and that does not incorporate propylene glycol or triclosan. The level of efficacy is greater than would have been expected based on the combination of the deodorizing actives propanediol, ethylhexylglycerin, and grapefruit seed extract.

The deodorant formulations of this invention, as will also be demonstrated below, also show excellent stability when used to manufacture deodorant stick product in accordance with the methods outlined herein.

FIG. 1 shows a sample formulation of the invention. A description of the manufacturing process for deodorant stick product follows. Taking the example of the particular ingredients listed in FIG. 1, the first step involves water, sodium bicarbonate, and sodium chloride being added to a mixing tank and agitated until dissolved. Hydroxyethylcellulose is then added and the mixture is further agitated until it is homogenous. While agitating, cornstarch and distarch phosphate acetate are added. The mixture is then agitated for at least 30 minutes, while heating to 65-75° C. The specified quantities of propanediol and glycerin are then added and agitated until homogenous, while maintaining the temperature at 65-75° C. Sodium stearate is then added with agitation until it is dissolved. The next step is to add the cetearyl alcohol, cetearyl glucoside, and behenyl alcohol while agitating, and simultaneously increasing the temperature to 85-90° C. The mixture is then agitated for 60 minutes at 85-90° C. Following this step, the mixture is then cooled to 76-80° C. while agitating. Finally, the ethylhexylglycerin is added along with the grapefruit seed extract, and any desired additives, essential oils, or perfumes. The mix is further agitated until it is homogenous, maintaining the temperature at 76-80° C., for 30-45 minutes.

The next step in the creation of the solid stick deodorant of the invention is the filling of the packaging. While agitating the bulk mixture and maintaining the temperature at 76-80° C., appropriate volumes of the mixture are poured into the top of appropriate empty plastic deodorant containers. A number of sources are available for such empty deodorant containers; containers purchased from Levlad Manufacturing were used. In an exemplary embodiment, a natural and stable deodorant stick product can be manufactured by the following method, with reference to the flowchart in FIG. 3. A deodorant container having an open top end and a closed bottom end is provided at step 102. The deodorant container has an interior for containing deodorant stick product. At step 104 the deodorant composition as manufactured according to the methods described above is provided. The deodorant composition is then poured into the interior of the deodorant container through the deodorant container's open top end 106. The open top end of the deodorant container is for dispensing deodorant product. The deodorant composition in the container is cooled until it is in a solid state 108. The open top end of the deodorant container is then covered with a lid 110.

Next, the filled deodorant containers are sent on a conveyor through two standard cooling boxes which have each been set at a temperature of 3-7° C. The filled deodorant containers reside for 30-40 minutes in each box at the indicated temperatures. The filled deodorant containers are subsequently conveyed in sequence to two more cooling boxes at temperatures of 8-12° C., again for periods of 30-40 minutes per box. At the end of this process, the product core temperature as it exits the fourth, final cooling box will be 25-35° C. The deodorant products may then be capped and labelled.

The foregoing steps constitute the preferred method by which the stick deodorant product of the present invention is made. However, it will be apparent to those of skill in the art that some variations may be applied to the steps in the method without departing from the scope of the invention. All such similar substitutes and modifications apparent to those skilled in the art are deemed to be within the spirit, scope, and concept of the invention as defined by the claims.

Following the above procedure, a natural deodorant solid stick product is formed by a method of top-filling. The product, when made by the above-described manufacturing method and top-fill procedure, has further shown to be more stable as compared to other deodorant products employing similar ingredients, but manufactured in accordance with a bottom-fill method. The stability of the product of the invention is revealed in the 12-week stability data presented in FIGS. 4-9.

FIG. 4 is a summary of a 12-week stability test. The formulation as set out in FIG. 1 was prepared in accordance with the manufacturing method described previously. The containers were weighed at the beginning of the test in order to provide a baseline, and samples were subsequently incubated at three different temperatures (4° C., 25° C., 45° C.) for a total of 12 weeks each. Once per week, each container was weighed, and the weight and percentage weight loss was recorded.

Similarly, FIG. 5 is a summary of the same 12-week stability test as in FIG. 4 using top-filled deodorant containers, the only difference being that the deodorant stick was given a domed top by the addition of a domed cap on the top of the cooling deodorant stick prior to solidification.

FIG. 6 is a summary of the same 12-week stability test as in FIGS. 4 and 5, however a modification of the manufacturing process was employed. Instead of pouring the molten deodorant into the containers from the top, the containers were filled from the bottom. Standard deodorant containers designed to be filled from the bottom were purchased from Levlad Manufacturing. In all other respects, the manufacturing method employed was identical to that set out previously.

Figure 7:
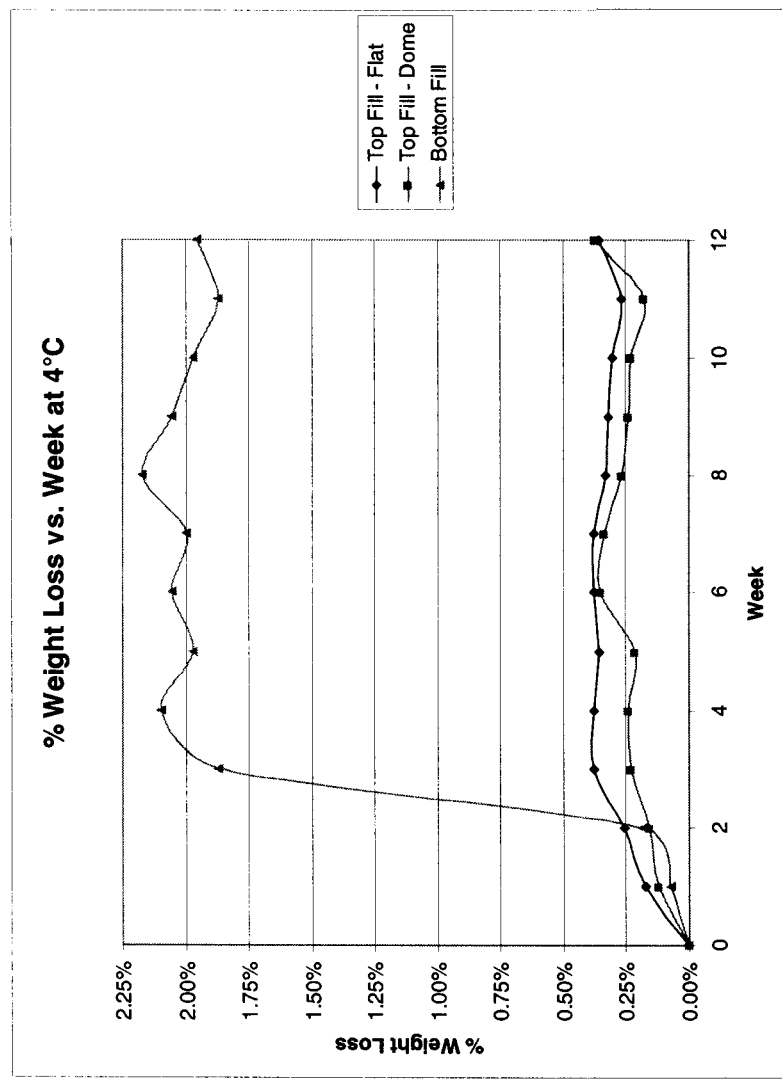
FIG. 7 is a graph showing stability results in terms of percentage weight loss for each of the types of packaging tested, at 4° C.
Figure 8:
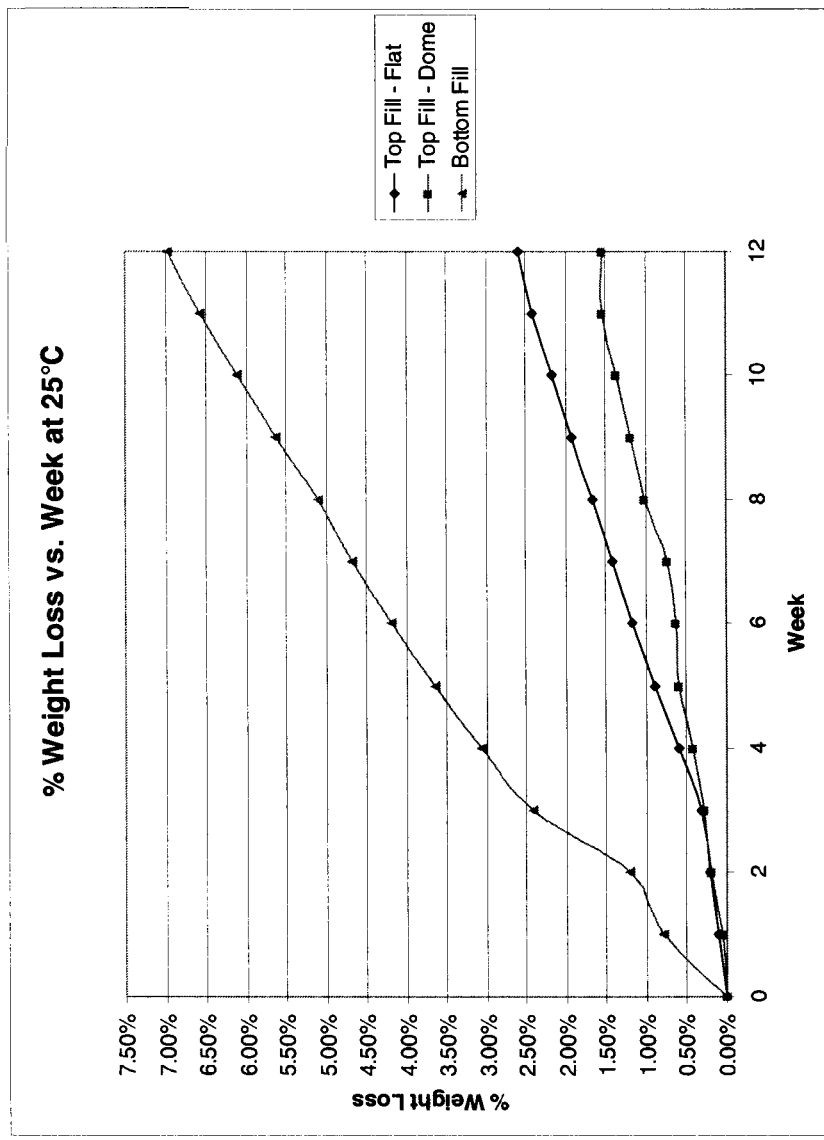
FIG. 8 is a graph showing stability results in terms of percentage weight loss for each of the types of packaging tested, at 25° C.
Figure 9:
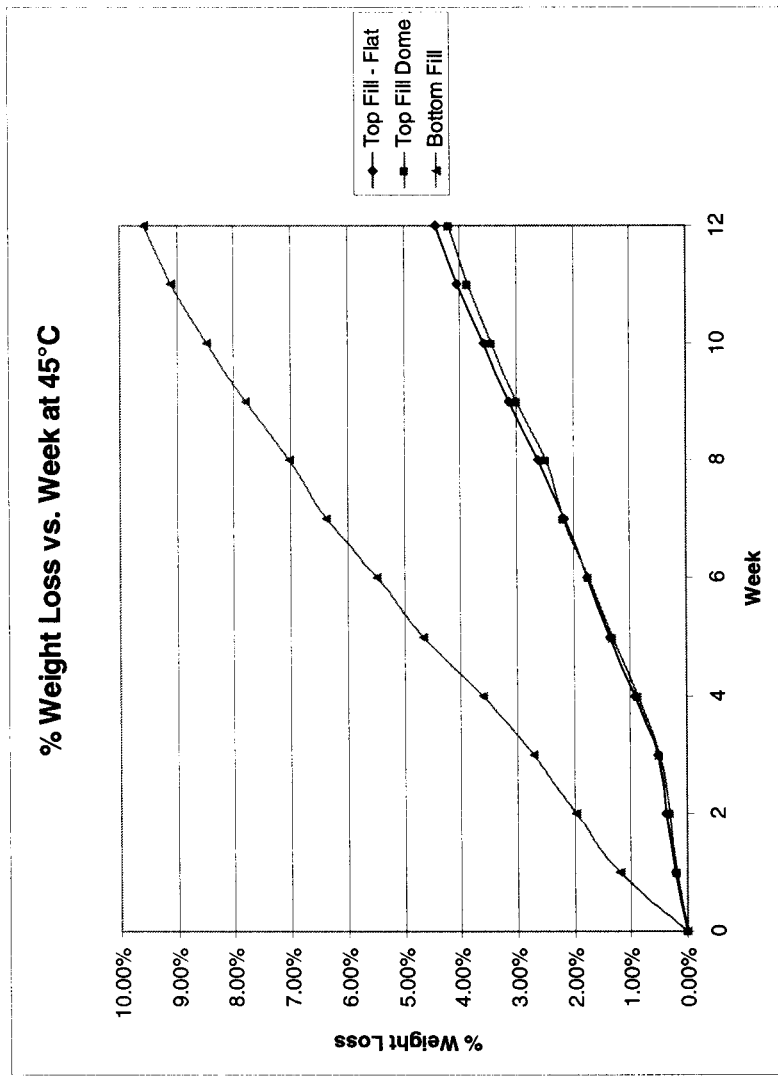
FIG. 9 is a graph showing stability results in terms of percentage weight loss for each of the types of packaging tested, at 45° C.

The differences in weight loss for the 12 week stability studies summarized in FIGS. 4, 5, and 6 are readily apparent when the data is graphed. FIGS. 7, 8, and 9 are graphs showing the percentage weight loss as a function of time for each of the tested samples and for each of the temperatures 4° C., 25° C., and 45° C. respectively. It can be seen that there is a dramatic difference in weight loss, and therefore stability of the solid deodorant product, at each of the test temperatures. It is evident that the two top-filled products had a slight degree of weight loss over the 12 weeks, which is to be expected. However, the extent of weight loss was dramatically different for the bottom-filled product, with approximately a two-eight fold difference in weight loss shown, depending on the incubation temperature.

This difference in weight loss translates to a significant difference in stability of the solid deodorant product. The differences have been confirmed by further testing, and reveals that for natural deodorant products such as of the formulation described herein, the particular manufacturing method, and in particular the method of forming the deodorant stick, makes a commercially significant difference in the ultimate product stability and shelf-life. The impact of the manufacturing method on product stability in this manner was surprising and has not been seen previously in the art.

As set out previously, a person of skill in the art may make adjustments to the steps used in the manufacturing process. In addition, further variations of the formulations are possible based on the variety of ingredients available in the prior art, as described above.

It should further be noted that when an amount, concentration or other parameter is given as a range or a list of upper and lower preferable values, it is to be understood as disclosing all ranges formed from any pair of any upper and lower limit. Where a range of numerical values is recited, unless otherwise stated, the range includes the endpoints thereof.

While the invention has been described with reference to specific embodiments thereof, it will be appreciated that numerous variations, modifications, and embodiments are possible. All such variations, modifications and embodiments are to be regarded as being within the spirit and scope of the invention.

What is claimed is the following:

1. A deodorant composition, comprising by weight, based on the total weight of the composition: from about 40-45% of propanediol; from about 0.1-0.6% of ethylhexylglycerin; from about 0.5-0.9% of grapefruit seed extract; from about 2-4% sodium stearate; about 20% glycerin; from about 0.01-0.9% distarch phosphate acetate; from about 0.01-0.3% of an emulsifier selected from the group consisting of cetearyl alcohol, cetearyl glucoside, benehyl alcohol, and mixtures thereof; about 0.1% of a thickening agent selected from the group consisting of hydroxyethylcellulose and sodium chloride, and mixtures thereof; and from about 0.01-0.05% of a clarifying agent, the composition being free from propylene glycol and triclosan.

2. The deodorant composition according to claim 1, wherein the sodium stearate is provided in an amount of about 4% by weight of the total composition.

3. The deodorant composition according to claim 1, further comprising about 0.1% benehyl alcohol by weight of the total composition.

4. The deodorant composition according to claim 1, comprising at least one further deodorizing active ingredient.

5. The deodorant composition according to claim 4, wherein the at least one further deodorizing active ingredient is present in an amount of about 0.1-5% by weight of the total composition.

6. A deodorant composition, comprising by weight, based on the total weight of the composition: about 45% propanediol; about 0.6% ethylhexylglycerin; about 0.9% grapefruit seed extract; about 4% sodium stearate; about 20% glycerin; from about 0.01-0.9% of distarch phosphate acetate; from about 0.01-0.3% of a mixture of cetearyl alcohol and cetearyl glucoside; about 0.1% benehyl alcohol; about 0.05% hydroxyethylcellulose, about 0.05% sodium chloride; and about 0.01% sodium bicarbonate, the composition being free from propylene glycol and triclosan.

7. A deodorant stick product made from the deodorant composition of claim 6, wherein said deodorant stick product is top-filled and finished with a dome, and which shows a cumulative weight loss of about 0.37% or less when stored for 12 weeks at 4° C., about 1.54% or less when stored for 12 weeks at 25° C., and about 4.2% or less when stored for 12 weeks at 45° C.

* * * * *